(12) United States Patent
Bangera et al.

(10) Patent No.: US 9,022,999 B2
(45) Date of Patent: May 5, 2015

(54) FLUID SPRAYING APPARATUSES, AND RELATED SYSTEMS AND METHODS

(75) Inventors: Mahalaxmi Gita Bangera, Renton, WA (US); Roderick A. Hyde, Redmond, WA (US); Jordin T. Kare, Seattle, WA (US); Eric C. Leuthardt, St. Louis, MO (US); Lowell L. Wood, Jr., Bellevue, WA (US)

(73) Assignee: Elwha, LLC, Bellevue, WA (US)

( * ) Notice: Subject to any disclaimer, the term of this patent is extended or adjusted under 35 U.S.C. 154(b) by 0 days.

(21) Appl. No.: 13/478,370

(22) Filed: May 23, 2012

(65) Prior Publication Data

US 2013/0296812 A1 Nov. 7, 2013

Related U.S. Application Data

(63) Continuation-in-part of application No. 13/462,203, filed on May 2, 2012.

(51) Int. Cl.
*A61M 35/00* (2006.01)
*A61B 18/02* (2006.01)

(52) U.S. Cl.
CPC ........................................ *A61B 18/02* (2013.01)

(58) Field of Classification Search
USPC .......................................................... 604/290
See application file for complete search history.

(56) References Cited

U.S. PATENT DOCUMENTS

| | | | |
|---|---|---|---|
| 3,534,739 A * | 10/1970 | Bryne | 606/22 |
| 4,043,341 A * | 8/1977 | Tromovitch | 606/22 |
| 4,348,873 A * | 9/1982 | Yamauchi et al. | 62/50.2 |
| 4,376,376 A | 3/1983 | Gregory | |
| 4,783,008 A | 11/1988 | Ikeuchi et al. | |
| 5,098,428 A * | 3/1992 | Sandlin et al. | 606/22 |
| 5,344,478 A | 9/1994 | Zurecki et al. | |
| 5,814,040 A * | 9/1998 | Nelson et al. | 606/9 |
| 5,997,530 A | 12/1999 | Nelson et al. | |
| 6,027,499 A * | 2/2000 | Johnston et al. | 606/22 |
| 6,171,301 B1 * | 1/2001 | Nelson et al. | 606/9 |
| 6,173,916 B1 | 1/2001 | Krone-Schmidt | |
| 6,226,996 B1 | 5/2001 | Weber et al. | |
| 6,248,103 B1 * | 6/2001 | Tannenbaum et al. | 606/9 |
| 6,514,244 B2 * | 2/2003 | Pope et al. | 606/9 |

(Continued)

OTHER PUBLICATIONS

U.S. Appl. No. 13/462,203, filed May 2, 2012, Bangera, et al.

(Continued)

*Primary Examiner* — Tatyana Zalukaeva
*Assistant Examiner* — Guy K Townsend
(74) *Attorney, Agent, or Firm* — Dorsey & Whitney LLP

(57) ABSTRACT

Embodiments disclosed herein are directed to fluid spraying apparatuses, and related systems and methods. The disclosed fluid spraying apparatuses may be used, for example, to spray a medically suitable fluid on a target region of a living subject such as for treating or removing tissue. In an embodiment, a fluid spraying apparatus includes a target designation unit having a target sensor configured to sense a target region of a living subject, a spray mechanism, and a controller. The spray mechanism includes at least one reservoir configured to hold fluid, and a spraying device operably coupled to the at least one reservoir, the spraying device configured to spray the fluid in the at least one reservoir onto the target region. The controller includes control electrical circuitry operably coupled to the spray mechanism and the target designation unit, and configured to control the spray mechanism responsive to the target sensor sensing the target region.

31 Claims, 13 Drawing Sheets

(56) References Cited

U.S. PATENT DOCUMENTS

| | | | |
|---|---|---|---|
| 6,635,053 B1* | 10/2003 | Lalonde et al. | 606/22 |
| 6,764,493 B1* | 7/2004 | Weber et al. | 606/131 |
| 6,996,951 B2* | 2/2006 | Smith et al. | 53/425 |
| 7,025,762 B2* | 4/2006 | Johnston et al. | 606/22 |
| 7,255,693 B1* | 8/2007 | Johnston et al. | 606/24 |
| 7,273,479 B2 | 9/2007 | Littrup et al. | |
| 7,282,060 B2* | 10/2007 | DeBenedictis et al. | 607/88 |
| 7,318,821 B2* | 1/2008 | Lalonde et al. | 606/22 |
| 7,769,469 B2* | 8/2010 | Carr et al. | 607/101 |
| 7,780,656 B2 | 8/2010 | Tankovich | |
| 7,921,657 B2 | 4/2011 | Littrup et al. | |
| 8,591,504 B2* | 11/2013 | Tin | 606/21 |
| 2001/0009997 A1* | 7/2001 | Pope et al. | 606/9 |
| 2002/0143323 A1* | 10/2002 | Johnston et al. | 606/21 |
| 2002/0161357 A1* | 10/2002 | Anderson et al. | 606/9 |
| 2004/0002704 A1* | 1/2004 | Knowlton et al. | 606/41 |
| 2005/0154380 A1* | 7/2005 | DeBenedictis et al. | 606/9 |
| 2005/0261753 A1 | 11/2005 | Littrup et al. | |
| 2006/0069306 A1 | 3/2006 | Banik et al. | |
| 2007/0118098 A1 | 5/2007 | Tankovich | |
| 2007/0276360 A1* | 11/2007 | Johnston et al. | 606/21 |
| 2008/0071332 A1* | 3/2008 | Nelson et al. | 607/89 |
| 2008/0119828 A1* | 5/2008 | Nelson et al. | 606/9 |
| 2008/0173028 A1 | 7/2008 | Littrup et al. | |
| 2008/0287943 A1 | 11/2008 | Weber et al. | |
| 2009/0192505 A1* | 7/2009 | Askew et al. | 606/21 |
| 2010/0057065 A1* | 3/2010 | Krimsky | 606/21 |
| 2010/0087806 A1 | 4/2010 | Da Silva et al. | |
| 2010/0111837 A1 | 5/2010 | Boyden et al. | |
| 2010/0111846 A1 | 5/2010 | Boyden et al. | |
| 2010/0111847 A1 | 5/2010 | Boyden et al. | |
| 2010/0111848 A1 | 5/2010 | Boyden et al. | |
| 2010/0111849 A1 | 5/2010 | Boyden et al. | |
| 2010/0111850 A1 | 5/2010 | Boyden et al. | |
| 2010/0111854 A1 | 5/2010 | Boyden et al. | |
| 2010/0111855 A1 | 5/2010 | Boyden et al. | |
| 2010/0111938 A1 | 5/2010 | Boyden et al. | |
| 2010/0112067 A1 | 5/2010 | Boyden et al. | |
| 2010/0112068 A1 | 5/2010 | Boyden et al. | |
| 2010/0113614 A1 | 5/2010 | Boyden et al. | |
| 2010/0113615 A1 | 5/2010 | Boyden et al. | |
| 2010/0114348 A1 | 5/2010 | Boyden et al. | |
| 2010/0114547 A1 | 5/2010 | Boyden et al. | |
| 2010/0119557 A1 | 5/2010 | Boyden et al. | |
| 2010/0121466 A1 | 5/2010 | Boyden et al. | |
| 2010/0143243 A1 | 6/2010 | Boyden et al. | |
| 2010/0152651 A1 | 6/2010 | Boyden et al. | |
| 2010/0152880 A1* | 6/2010 | Boyden et al. | 700/117 |
| 2010/0163576 A1 | 7/2010 | Boyden et al. | |
| 2010/0168725 A1* | 7/2010 | Babkin et al. | 606/21 |
| 2010/0168900 A1 | 7/2010 | Boyden et al. | |
| 2010/0185174 A1 | 7/2010 | Boyden et al. | |
| 2010/0187728 A1 | 7/2010 | Boyden et al. | |
| 2010/0249765 A1* | 9/2010 | Johnston | 606/21 |
| 2010/0274236 A1 | 10/2010 | Krimsky | |
| 2010/0286791 A1 | 11/2010 | Goldsmith | |
| 2011/0024132 A1 | 2/2011 | Pettit | |
| 2011/0168808 A1 | 7/2011 | Mitch | |
| 2011/0230753 A1 | 9/2011 | Mahon et al. | |

OTHER PUBLICATIONS

PCT International Search Report; International App. No. PCT/US2013/039198; Aug. 15, 2013; pp. 1-2.

PCT International Search Report; International App. No. PCT/US2013/039202; Aug. 15, 2013; pp. 1-3.

* cited by examiner

FLUID SPRAYING APPARATUSES, AND RELATED SYSTEMS AND METHODS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/462,203, entitled FLUID SPRAYING APPARATUSES, AND RELATED SYSTEMS AND METHODS, naming Mahalaxmi Gita Bangera, Roderick A. Hyde, Jordin T. Kare, Eric C. Leuthardt, and Lowell L. Wood, Jr. as inventors, filed 2 May 2012, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Embodiments disclosed herein are directed to fluid spraying apparatuses, and related systems and methods. The disclosed fluid spraying apparatuses include a target designation unit for designating a target region to be sprayed and a spray mechanism that is controllable responsive to sensing feedback from the target designation unit and other optional sensor(s) such as a distance sensor. The disclosed fluid spraying apparatuses may be used, for example, to spray a medically suitable fluid on a target region of a living subject such as for treating or removing tissue from a living subject.

In an embodiment, a fluid spraying apparatus includes a target designation unit having a target sensor configured to sense a target region of a living subject, a spray mechanism, and a controller. The spray mechanism includes at least one reservoir configured to hold fluid, and a spraying device operably coupled to the at least one reservoir that is configured to spray the fluid in the at least one reservoir onto the target region. The controller includes control electrical circuitry operably coupled to the spray mechanism and the target designation unit. The control electrical circuitry is configured to control the spray mechanism responsive to the target sensor sensing the target region.

In an embodiment, a method is disclosed that is directed to spraying fluid onto a designated target region of a living subject. The method includes sensing a target region of a living subject with a target designating unit, designating the target region, and spraying fluid onto the target region so designated from a spray mechanism of a fluid spraying apparatus.

In an embodiment, a system is disclosed. The system includes a target designation unit including a target sensor configured to sense a target region of a living subject, and a fluid spraying apparatus operably coupled to the target designation unit. The fluid spraying apparatus including a spray mechanism having at least one reservoir configured to hold fluid, a spraying device operably coupled to the at least one reservoir, and a computer operably coupled to the spray mechanism and the target designation unit. The spraying device is configured to spray the fluid in the at least one reservoir onto the target region. The computer includes memory storing instructions for controlling the spray mechanism responsive to the target sensor sensing the target region.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other living subject matter described herein will become apparent after reading the teachings set forth herein.

Figure 1:
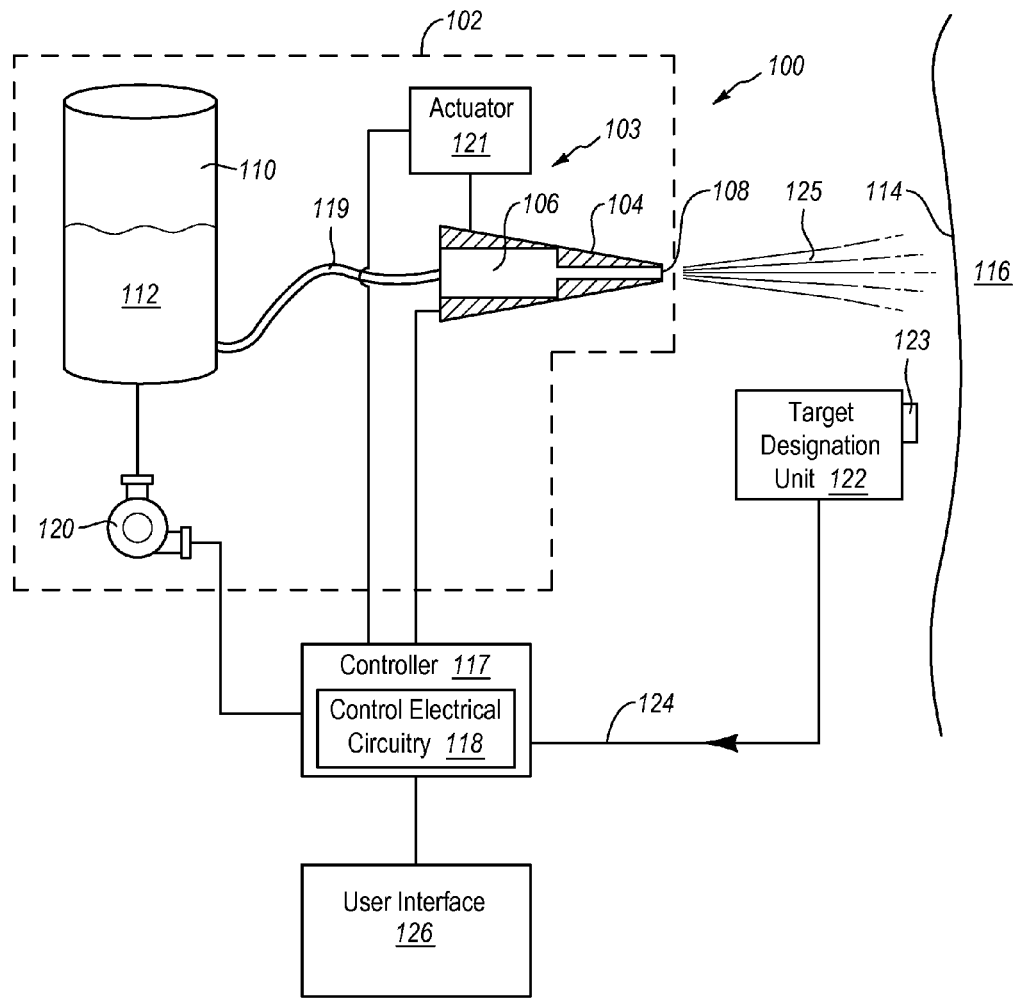
FIG. 1 is a schematic diagram of an embodiment of a fluid spraying apparatus including a target designation unit for designating a target region of a living subject to be sprayed with fluid.

FIG. 10 is a schematic diagram of an embodiment of a fluid spraying apparatus including a plurality of reservoirs from which fluid may be selectively sprayed onto a target region of a living subject.

FIG. 11 is a schematic diagram of an embodiment of a fluid spraying apparatus that includes a target designation unit and at least one distance sensor.

FIG. 12 is a flow diagram of an embodiment of an operating method that may be implemented using any of the fluid spraying apparatuses disclosed herein.

FIG. 13 is a schematic diagram of an embodiment of a system including a fluid spraying apparatus and a computer for controlling the fluid spraying apparatus.

DETAILED DESCRIPTION

Embodiments disclosed herein are directed to fluid spraying apparatuses, and related systems and methods. The disclosed fluid spraying apparatuses include a target designation unit for designating a target region to be sprayed and a spray mechanism that is controllable responsive to sensing feedback from the target designation unit and other optional sensor(s) such as a distance sensor. The disclosed fluid spraying apparatuses may be used, for example, to spray a medically suitable fluid on a target region of a living subject such as for treating or removing tissue from a living subject during cryosurgery or pyrosurgery.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be strictly limiting. Other embodiments may be utilized, and other changes may be made, without departing from the spirit or scope of the living subject matter presented herein.

FIG. 1 is a schematic diagram of an embodiment of a fluid spraying apparatus 100. The fluid spraying apparatus 100 is suitable for spraying a medically suitable fluid onto a target region of a living subject for a variety of uses. For example, the sprayed fluid may be employed for treating or removing internal or external tissue of a living subject. The fluid spraying apparatus 100 may be configured to be handheld by a user, or may be supported by a manually or an automatically controlled mount. The fluid spraying apparatus 100 includes a spray mechanism 102 having a spraying device 103 with an adjustable spray nozzle 104 (e.g., an atomizing adjustable spray nozzle, a pressure-swirl spray nozzle, or other suitable nozzle). The adjustable spray nozzle 104 includes a fluid delivery passageway 106 extending therethrough that terminates at one end of the adjustable spray nozzle 104 as an output orifice 108 from which fluid may be sprayed as a spray 125.

The spray mechanism 102 of the fluid spraying apparatus 100 further includes at least one reservoir 110 holding fluid 112 therein. For example, the reservoir(s) disclosed herein may be a canister, a flexible bag, a receptacle, or other suitable container for holding fluid. The fluid 112 may include at least one of a liquid, a gas, or an aerosol. As an example, the fluid 112 may include a cryogen or a fluid having a temperature greater than about 45° C. (i.e., a pyrofluid). When the fluid 112 includes cryogen or a pyrofluid, the reservoir 110 may be appropriately thermally insulated as needed. Suitable examples of cryogen include at least one of nitrogen, carbon dioxide, a fluorocarbon, ethynol, or ethanol.

The reservoir 110 is in fluid communication with the fluid delivery passageway 106 of the adjustable spray nozzle 104 via one or more fluid conduits 119 (e.g., tubing or passageways formed in a substrate). The reservoir 110 is in fluid communication with the fluid delivery passageway 106 of the adjustable nozzle assembly 104 such that the fluid 112 may be received by the fluid delivery passageway 106 of the adjustable nozzle assembly 104 and sprayed from the output orifice 108 onto a target region 114 of a living subject 116, such as a human or non-human animal living subject. For example, the target region 114 may be internally or externally located on the living subject 116.

The spray mechanism 102 further includes a pump 120 operably coupled to the reservoir 110 and a controller 117 including control electrical circuitry 118. For example, the pump 120 may be configured as an electronically-activated pneumatic pump, an electronically-activated hydraulic pump, or an electronically-activated reciprocating pump (e.g., a plunger pump or a diaphragm pump). The pump 120 is configured to pump the fluid 112 from the reservoir 110 to the fluid delivery passageway 106 of the adjustable nozzle assembly 104 via the one or more fluid conduits 119. As will be discussed in more detail below, the control electrical circuitry 118 of the controller 117 may be operably coupled to the adjustable spray nozzle 104, in addition to the pump 120, for controlling the operation thereof.

In the illustrated embodiment, the spray mechanism 102 further includes an actuator 121 operably coupled to the spraying device 103 and the controller 117. For example, the actuator 121 may include at least one of a piezoelectric actuator, a shape-memory-alloy actuator, or an electromagnetic actuator that is configured to move the spraying device 103 so that the spray 125 can be selectively directed at the target region 114. As will be discussed in more detail below, responsive to instructions from the control electrical circuitry 118 of the controller 117, the actuator 121 may move the spraying device 103 so that the spray 125 is directed at the target region 114 designated. However, in another embodiment, the actuator 121 may be omitted and the spraying device 103 may be manually steered by a user.

A target designation unit 122 including a target sensor 123 is further operably coupled to the control electrical circuitry 118 of the controller 117. The target designation unit 122 is positioned and configured to sense information about the target region 114 and output one or more sensing signals 124 to the control electrical circuitry 118 of the controller 117 indicative (e.g., encoding) of the information. As will be discussed in more detail below, the target sensor 123 may include an image sensor (e.g., an electronic camera, machine vision system, or other suitable electronic imaging device), a motion sensor (e.g., a MEMS gyroscope motion sensor or inertial sensor), a temperature sensor (e.g., an infrared sensor or other contactless temperature sensor), or other suitable target sensor.

A user interface 126 (e.g., a keypad, monitor, touch screen, voice command recognition, or combinations thereof) is provided that is operably coupled to the control electrical circuitry 118 of the controller 117. The user interface 126 is configured to allow a user to designate the target region 114 via user input responsive to sensing information received from the target designation unit 122 or change operational parameters of the spray mechanism 102.

In operation, the target sensor 123 of the target designation unit 122 senses information about the target region 114 of the living subject 116 and outputs the one or more sensing signals 124 to the control electrical circuitry 118 of the controller 117 indicative of the information. In an embodiment, the user may designate/select the target region 114 via the user interface 126 before or after the spray mechanism 102 outputs the spray 125. In an embodiment, responsive to the user designating the target region 114, the control electrical circuitry 118 of the controller 117 may activate the spray mechanism 102 and direct the actuator 121 to move the spraying device 103 so that the fluid 112 is sprayed from the spraying device 103 as the spray 125 onto the target region 114 so designated. For example, the control electrical circuitry 118 may be configured to control the spray mechanism 102 to prevent the spray mechanism 102 from spraying outside the target region 114 that is designated so that the spray 125 is substantially maintained directed at the target region 114. In an embodiment, the spray mechanism 102 may be automatically activated responsive to the control electrical circuitry 118 of the controller 117 receiving the one or more sensing signals 124 such as when the one or more sensing signals 124 are indicative of the target region 114 being correct. In other embodiments, after the spray mechanism 102 has sprayed the target region 114, the user may designate the sprayed target region 114 as correct via the user interface 126 so that the control electrical circuitry 118 maintains the spraying device 103 directing the spray 125 onto the target region 114 designated as correct.

The control electrical circuitry 118 may also determine one or more operational characteristics of the spray mechanism 102 (e.g., the adjustable spray nozzle 104, the at least one reservoir 110, or the pump 120) to be adjusted at least partially based on the information sensed or perceived by the target designation unit 122, adjusts the one or more operational characteristics of the spray mechanism 102 at least partially based on the determined one or more operational characteristics so that the target region 114 may be more accurately targeted, and directs the adjusted spray mechanism 102 configured with the one or more adjusted operational characteristics to spray the fluid 112 as a spray 125 onto the target region 114 so designated responsive to the pump 120 delivering the fluid 112 to the spray mechanism 102. For example, the one or more operational characteristics include at least one of pressure of the spray 125, droplet size of the spray 125, or geometry of the spray 125.

As further explained below, responsive to the one or more sensing signals 124, the control electrical circuitry 118 may direct altering a number of different operational characteristics of the spray mechanism 102 to enable more accurate targeting of the target region 114 with the spray 125. For example, during operation, the control electrical circuitry 118 may direct the adjustable spray nozzle 104 to alter a spray width of the spray 125 responsive to receiving the one or more sensing signals 124. As another example, during operation, the control electrical circuitry 118 may direct the pump 120 to alter a fluid pressure of the fluid 112 sprayed therefrom as the spray 125 responsive to receiving the one or more sensing signals 124. Altering the fluid pressure may be effected by increasing or decreasing the pressure exerted on the fluid 112 in the reservoir 110 by the pump 120. As yet another example, during operation, the control electrical circuitry 118 may direct the adjustable spray nozzle 104 to alter a fluid focus thereof responsive to receiving the one or more sensing signals 124. As yet another example, during operation, the control electrical circuitry 118 may direct the spray mechanism 102 to alter a droplet size of the spray 125 responsive to receiving the one or more sensing signals 124 by increasing or decreasing the pressure exerted on the fluid 112 in the reservoir 110 by the pump 120. As yet a further example, during operation, the control electrical circuitry 118 may direct adjusting the adjustable spray nozzle 104 to substantially maintain a target arrival diameter of the spray 125 responsive to receiving the one or more sensing signals 124.

In an embodiment, the control electrical circuitry 118 is configured to direct the spray mechanism 102 to stop spraying the fluid 112 responsive to a specified operational condition. For example, the specified operational condition includes at least one of spray time, the distance being outside a specified range as sensed by the distance sensor 122, or the distance changing at a rate exceeding a maximum rate as sensed by the distance sensor 122. In other embodiments, the control electrical circuitry 118 directs the spray mechanism 102 to intermittently spray the fluid 112 onto the target region 114. As previously discussed, the specified operational conditions may be pre-programmed into the control electrical circuitry 118 or set by the user.

The instructions that the control electrical circuitry 118 employs for directing and controlling operation of the spray mechanism 102 (e.g., selected fluid focus, target arrival diameter, or other spray characteristics) or the actuator 121 may be pre-programmed in the control electrical circuitry 118 without user input, programmed by the user, or implemented by hardware. For example, the programming may be effected via at least one of software, firmware, programmable logical devices, or other technique for controlling the spray mechanism 102 or components thereof in a selected manner.

Figure 2:
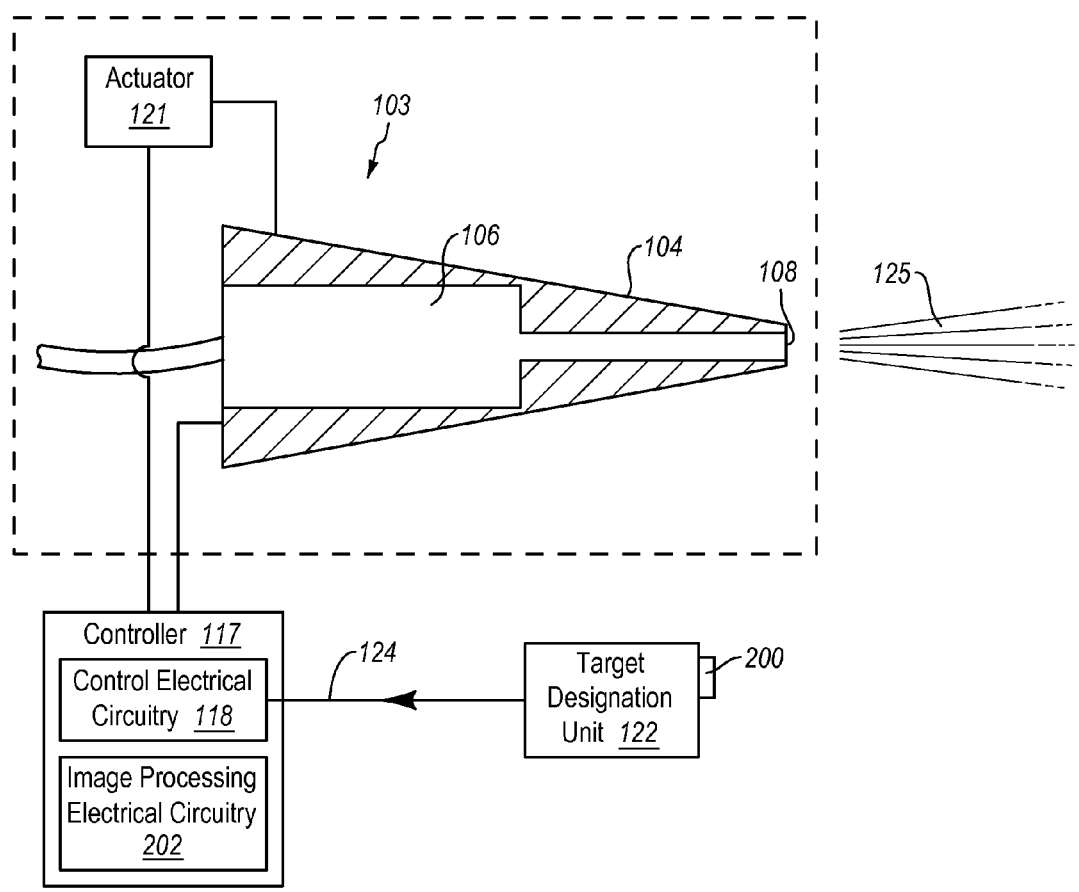
FIG. 2 is a schematic diagram of the fluid spraying apparatus shown in FIG. 1 in which a target sensor thereof includes an image sensor according to an embodiment.

FIG. 2 is a schematic diagram of the fluid spraying apparatus 100 shown in FIG. 1 in which the target sensor 123 includes an image sensor 200 according to an embodiment. As previously discussed, the image sensor 200 may include at least one of an electronic camera, a machine vision system, or other suitable electronic imaging device. For example, the image sensor 200 may be positioned and configured to image subsurface features of the target region 114, such as vasculature of the target region 114, which can be affected by the spray 125.

In operation, the image sensor 200 of the target designation unit 122 captures visual information about the target region 114 of the living subject 116 and outputs the one or more sensing signals 124 to the control electrical circuitry 118 of the controller 117 indicative of the visual information. In an embodiment, the user may designate/select the target region 114 via the user interface 126. For example, the visual information about the target region 114 may be displayed on the user interface 126 (e.g., a touch screen) and the user may designate the target region 114 to be sprayed by the spray 125. Responsive to the user designating the target region 114, the control electrical circuitry 118 of the controller 117 may activate and direct the spray mechanism 102 to cause spraying of the fluid 112 from the spraying device 103 as the spray 125 onto the target region 114. In other embodiments, the spray mechanism 102 may be automatically activated responsive to the control electrical circuitry 118 of the controller 117 receiving the one or more sensing signals 124 indicative of the visual information.

Figure 3:
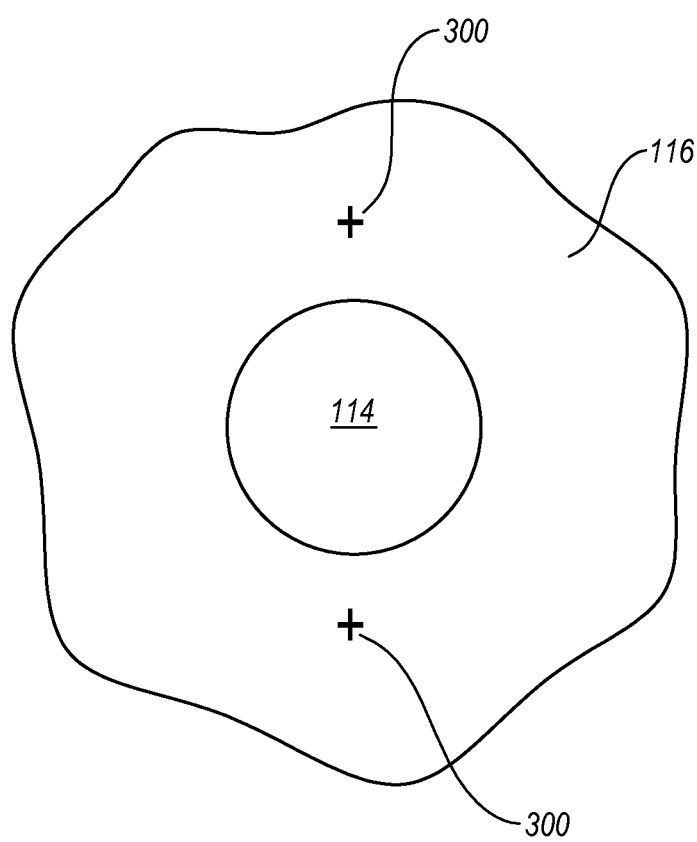
FIG. 3 is a schematic diagram of a target region defined by an indicator or a feature recognizable by the image sensor of FIG. 2.

As discussed above, in some embodiments, the image sensor 200 may be configured to recognize at least one feature of the target region 114 or at least one feature that at least partially surrounds the target region 114 to indicate a position thereof such as fiducial marks or other indicator. FIG. 3 is a schematic diagram of the target region 114 defined by indicators 300 recognizable by the image sensor 200 of FIG. 2. For example, the indicators 300 may be marks (e.g., crosses or other indicia) made on the living subject 116 with ink, tape, or other material suitable to mark a region of the living subject 116 that borders, at least partially surrounds, or indicates a specific portion of the target region 114 to be sprayed. The control electrical circuitry 118 may be configured to recognize the indicators 300 and direct the spray mechanism 102 to spray the fluid 112 as the spray 125 at the target region 114 between the indicators 300. For example, the controller 117 may include image processing electrical circuitry 202 coupled to the target designation unit 122 to receive the one or more sensing signals 124 therefrom and coupled to the control electrical circuitry 118. The image processing electrical circuitry 202 may be configured to recognize or process specific images captured by the image sensor 200.

Figure 4:
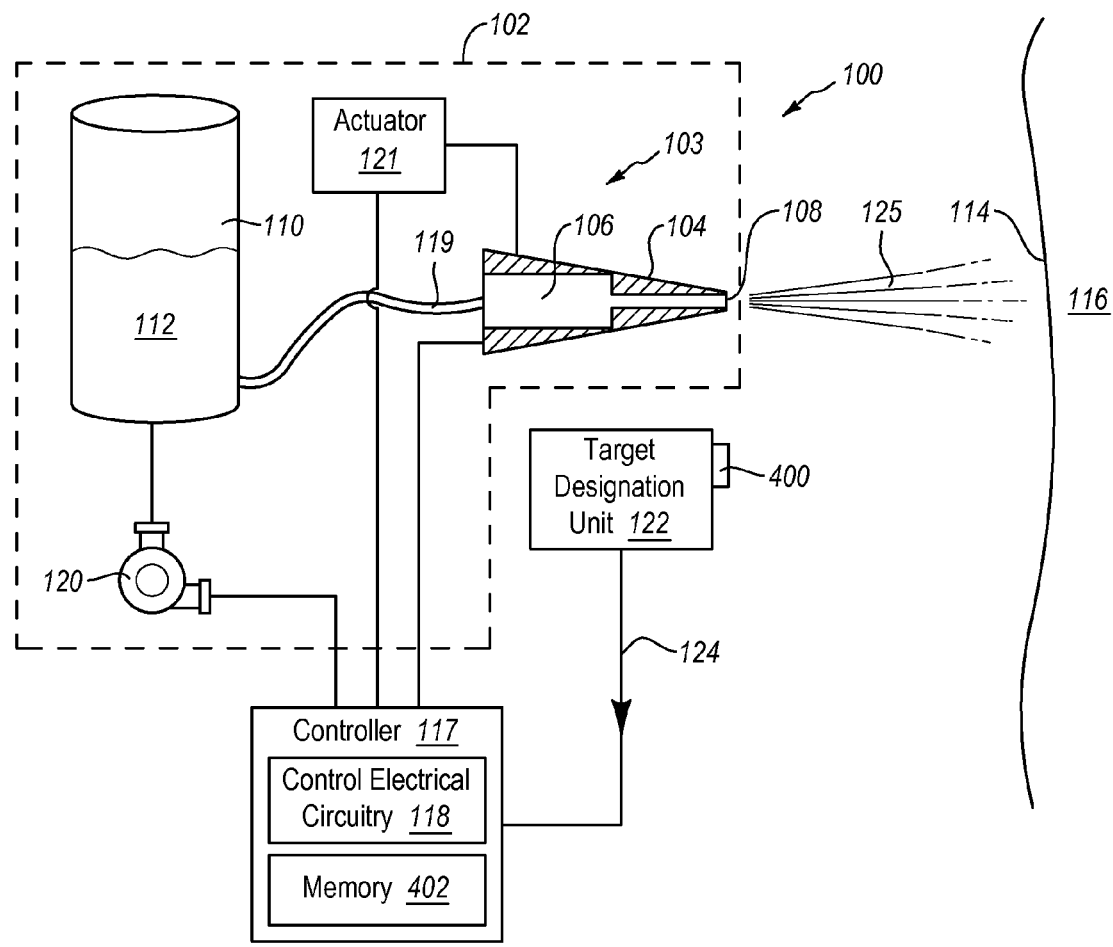
FIG. 4 is a schematic diagram of the fluid spraying apparatus shown in FIG. 1 in which a target sensor thereof includes a motion sensor according to an embodiment.

FIG. 4 is a schematic diagram of the fluid spraying apparatus 100 shown in FIG. 1 in which the target sensor 123 includes a motion sensor 400 according to an embodiment. The motion sensor 400 may be configured to sense motion of the spray mechanism 102 (e.g., the spraying device 103) or the target region 114, and output the one or more sensing signals 124 (i.e., one or more motion sensing signals) encoding data related to the sensed motion to the controller 117. For example, the motion sensor 400 may include at least one of a MEMS gyroscope sensor, an inertial sensor, or a physical sensor configured to output the one or more motion signals.

In such an embodiment, the control electrical circuitry 118 may be configured to instruct the spray mechanism 102 to direct the spray 125 onto the target region 114 responsive to the data. As the motion of the spray mechanism 102 is sensed, the operational characteristics of the spray mechanism 102 may be appropriately adjusted by the control electrical circuitry 118, as needed or desired, so that the spray 125 accurately targets the desired target region 114 responsive to the sensed motion of the spray mechanism 102. For example, the control electrical circuitry 118 may instruct the actuator 121 to appropriately steer the adjustable spray nozzle 104 of the spray mechanism 102 to account for motion of the spray mechanism 102 or the target region 114 so that the spray 125 is accurately directed onto the target region 114 so designated. In another embodiment, the control electrical circuitry 118 may instruct the spray mechanism 102 to direct the spray 125 to counteract effects of motion of the spray mechanism 102 relative to the target region 114. The desired target region 114 may be a specific target that has been preprogrammed into the controller 117 or designated by the user via the user interface 126 in conjunction with, for example, the image sensor 200 (see FIG. 2). In some embodiments, the controller 117 includes memory 402 configured to store the data related to the sensed motion for further review or analysis at a later time.

Figure 5:
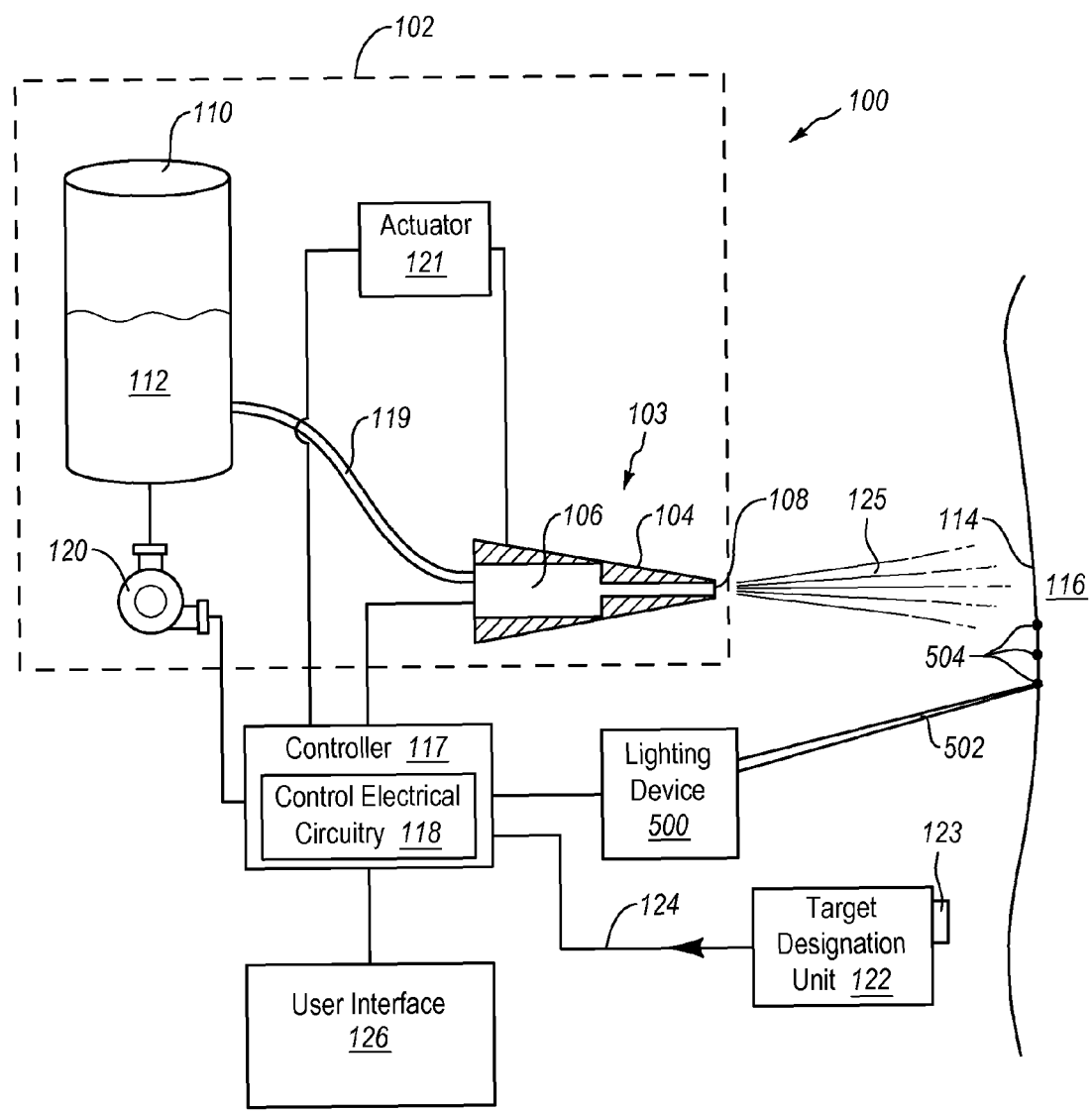
FIG. 5 is a schematic diagram of the fluid spraying apparatus shown in FIG. 1 associated with a lighting device configured to designate the target region on the living subject with light that is detectable by the target designation unit according to an embodiment.

FIG. 5 is a schematic diagram of the fluid spraying apparatus 100 shown in FIG. 1 that further includes a lighting device 500 configured to designate the target region 114 on the living subject 116 with light 502 that is detectable by the target designation unit 122 according to an embodiment. For example, the lighting device 500 may include a light emitting diode, a laser, a laser diode, or other suitable light source configured to output the light 502 at the target region 114. As merely one example, the lighting device 500 may be configured to output the light 502 as a beam of light that may be controllably scanned across the target region 114. The lighting device 500 may be operably coupled to the control electrical circuitry 118 of the controller 117 and the operation of the lighting device 502 may be controlled by the control electrical circuitry 118.

In operation, the user may direct the lighting device 500 (via the user interface 126) to output the light 502 so that the target region 114 is illuminated. The target sensor 123 of the target designation unit 122 senses or perceives the illuminated target region 114 and outputs the one or more sensing signals 124 indicating that the target region 114 has been illuminated to the control electrical circuitry 118 of the controller 117. For example, the target sensor 123 may be any of the aforementioned image sensors or other photosensitive detector. The control electrical circuitry 118 directs the spray mechanism 102 to spray the fluid 112 as the spray 125 accurately onto the illuminated target region 114.

In the illustrated embodiment, the control electrical circuitry 118 may direct the spray mechanism 102 to spray a selected number of sub-regions 504 within the target region 114 with the spray 125. For example, the lighting device 500 may selectively and sequentially illuminate each of the sub-regions 504 with the light 502, and the spray mechanism 102 may be directed by the control electrical circuitry 118 to selectively spray each sub-region 504 upon being illuminated. In an embodiment, the lighting device 500 may selectively illuminate only one of the sub-regions 504 with the light 502, and the spray mechanism 102 may be directed by the control electrical circuitry 118 to selectively spray only the single sub-region 504 that is illuminated. In an embodiment, the control electrical circuitry 118 may direct the spray mechanism 102 to spray substantially the entire the target region 114 with the spray 125 as a substantially continuous swept spray that may, for example, sweep across the target region 114 from one side to an opposing side.

Figure 6:
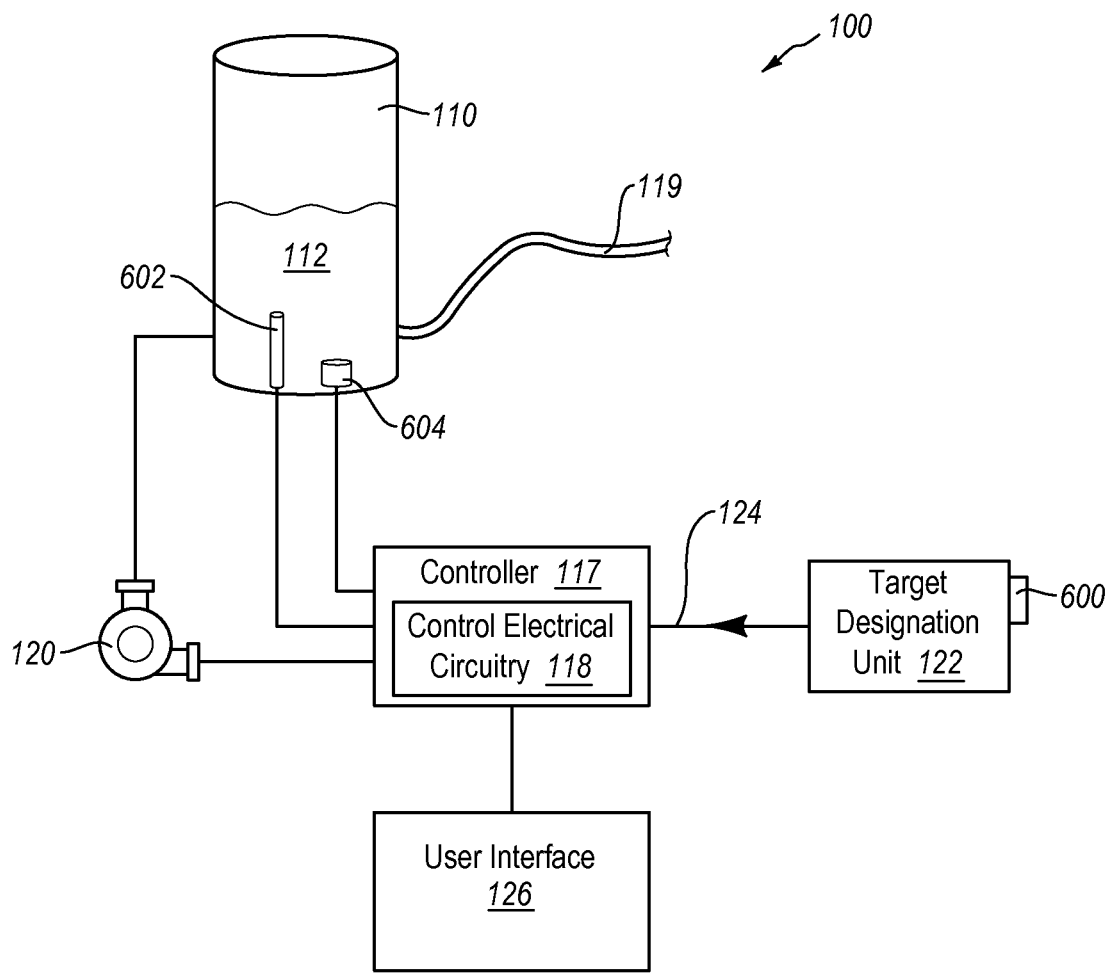
FIG. 6 is a schematic diagram of the fluid spraying apparatus shown in FIG. 1 in which a target sensor thereof includes a temperature sensor according to an embodiment.

FIG. 6 is a schematic diagram of the fluid spraying apparatus 100 shown in FIG. 1 in which the target sensor 126 includes a temperature sensor 600 according to an embodiment. The temperature sensor 600 may be configured to sense a temperature of the target region 114 and communicate the temperature to the control electrical circuitry 118 via the one or more sensing signals 124 (i.e., one or more temperature sensing signals). The temperature sensor 802 may be chosen from a number of available sensors, such as at least one of an infrared sensor, a microwave thermal sensor, a thermal imaging sensor, or other suitable device configured to measure temperature of the target region 114 without physically contacting the target region 114. For example, in an embodiment, the temperature sensor 600 may include a thermal imaging sensor configured for both visual imaging of the target region 114 (as in the embodiment shown in FIG. 2) so that the user can designate the target region 114 via the user interface 126 and also measure temperature of the target region 114.

The control electrical circuitry 118 is configured to direct the spray mechanism 102 to spray the fluid 112 onto the target region 114 responsive to the temperature sensed by the temperature sensor 600 as indicated by the one or more sensing signals 124. For example, in an embodiment, the control electrical circuitry 118 is configured to direct the spray mechanism 102 to spray the fluid 112 on the target region 114 until a selected temperature of the target region 114 is sensed by the temperature sensor 802.

In an embodiment, the temperature sensor 600 senses a temperature of each of a plurality of regions of the living subject 116 that includes the target region 114, and the user may designate the target region 114 by selecting the target region 114 from among the plurality of regions at least partially based on the temperature thereof. In another embodiment, the temperature sensor 600 senses a temperature of the target region 114, and the control electrical circuitry 118 directs the spray mechanism 102 to spray the fluid 112 onto the target region 114 until a selected temperature of the target region 114 is sensed with the temperature sensor 600.

In an embodiment (as illustrated), a heating or cooling element 602 (e.g., a resistive heating element or Peltier cell) may be disposed in the reservoir 110 in contact with the fluid 112. A temperature sensor 604 (e.g., a thermal couple) may also be disposed in the reservoir 110 in the fluid 112 and configured to measure a temperature of the fluid 112. The heating or cooling element 602 and the temperature sensor 604 may be operably coupled to the control electrical circuitry 118 of the controller 117 so that the heating or cooling element 602 may controllably heat or cool the fluid 112 to a selected temperature based on the temperature sensed by the temperature sensor 604.

In an embodiment, the control electrical circuitry 118 is configured to direct the spray mechanism 102 to spray the fluid 112 on the target region 114 so that a selected temperature profile is imposed on the target region 114. For example, the control electrical circuitry 118 may be configured to direct the spray mechanism 102 to alter at least one of a spray direction of the spray 125 or a spray divergence of the spray 125 for controlling the selected temperature profile or responsive to the selected temperature profile being measured by the temperature sensor 600. Such a temperature profile may be configured as a microwave temperature sensor that outputs microwave energy and determines the temperature from the reflected and/or absorbed microwave energy. For example, the temperature profile may be a three-dimensional temperature profile, a temperature-time profile, a temperature-depth profile, or a temperature-time-depth profile. As merely one example, a surface temperature of the target region 114 may be maintained at a selected temperature for a selected period of time. Based on the temperature measurement from the temperature sensor 600, the control electrical circuitry 118 may heat or cool the fluid 112 via the heating or cooling element 602 to be sprayed so that the selected temperature profile can be imposed on the target region 114. As another example, a selected temperature-depth profile may be imposed on the target region 114 so that tissue thereof may be frozen to a selected depth.

The temperature profile may be controlled or imposed by various techniques. For example, the control electrical circuitry 118 may be configured to direct adjusting of the adjustable spray nozzle 104 to alter at least one of a spray rate of the fluid 112 or a pulse spray frequency of the fluid 112 for controlling the selected temperature profile. As another example, the control electrical circuitry 118 may heat or cool the fluid 112 via the heating or cooling element 602 to be spray so that the selected temperature profile can be imposed on the target region 114.

In an embodiment, the target designation unit 122 including the temperature sensor 600 may be remote from the spray mechanism 102 and the spraying device 103. In other embodiments, the target designation unit 122 including the temperature sensor 600 may be integrated (e.g., mounted) with the spraying device 103.

In other embodiments, the operation of the spray mechanism 102 may be terminated responsive to feedback from the temperature sensor 600 or other additional sensors. For example, the control electrical circuitry 118 may terminate operation of the spray mechanism 102 responsive to at least one of a temperature sensed by the temperature sensor 600, tissue damage or changes of the target region 114 sensed by an additional sensor (e.g., an image sensor, an ultrasonic sensor, or a chemical sensor), or optical characteristics of the target region sensed by an optical sensor (e.g., an infrared sensor).

Figures 7A, 7B:
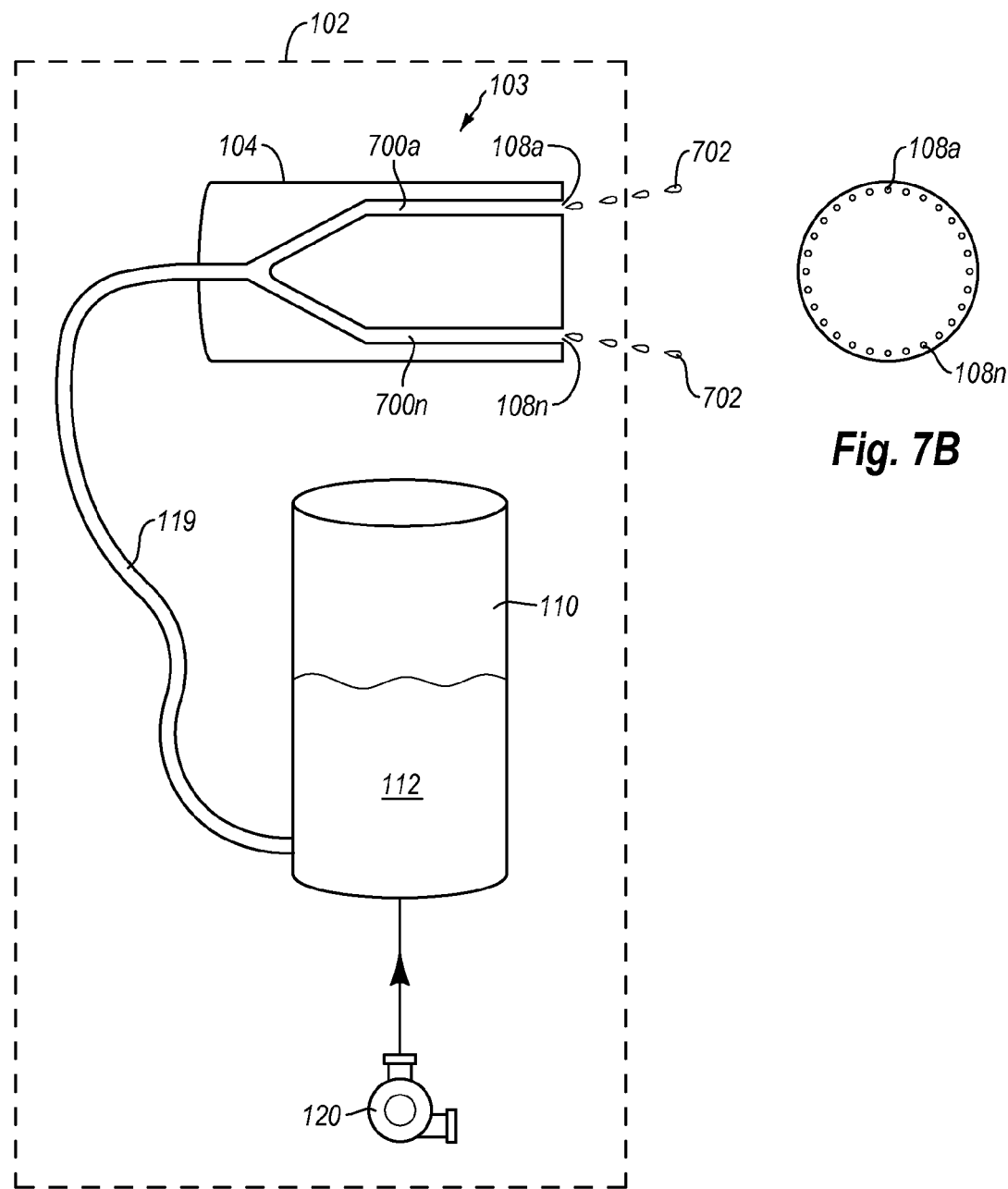
FIG. 7A is a partial schematic diagram of the fluid spraying apparatus shown in FIG. 1 in which a spray mechanism includes a spray nozzle configured to spray droplets according to an embodiment.
FIG. 7B is a plan view of the spray nozzle shown in FIG. 7A.

FIGS. 7A and 7B are partial schematic diagram and plan views, respectively, of the spray mechanism 102 of the fluid spraying apparatus 100 shown in FIG. 1 according to an embodiment. The adjustable spray nozzle 104 includes a plurality of output orifices 108a-108n through and from which the fluid 112 is sprayed during operation. In the illustrated embodiment, the plurality of output orifices 108a-108n may be circumferentially distributed, but other configurations may be employed. Each of the plurality of output orifices 108a-108n is in fluid communication with a corresponding fluid conduit 700a-700n, all of which may be collectively in fluid communication with the one or more fluid conduits 119 coupled to the reservoir 110.

During operation, a droplet size of droplets 702 sprayed from the plurality of output orifices 108a-108n may be controlled by varying the pressure of the fluid 112 pumped to the corresponding fluid conduits 700a-700n associated with each of the plurality of output orifices 108a-108n responsive to the one or more sensing signals 124 (FIG. 1). For example, increasing the pump pressure from the pump 120 may decrease the droplet size of the droplets 702, while decreasing the pump pressure from the pump 120 may relatively increase the droplet size of the droplets 702.

Figure 8:
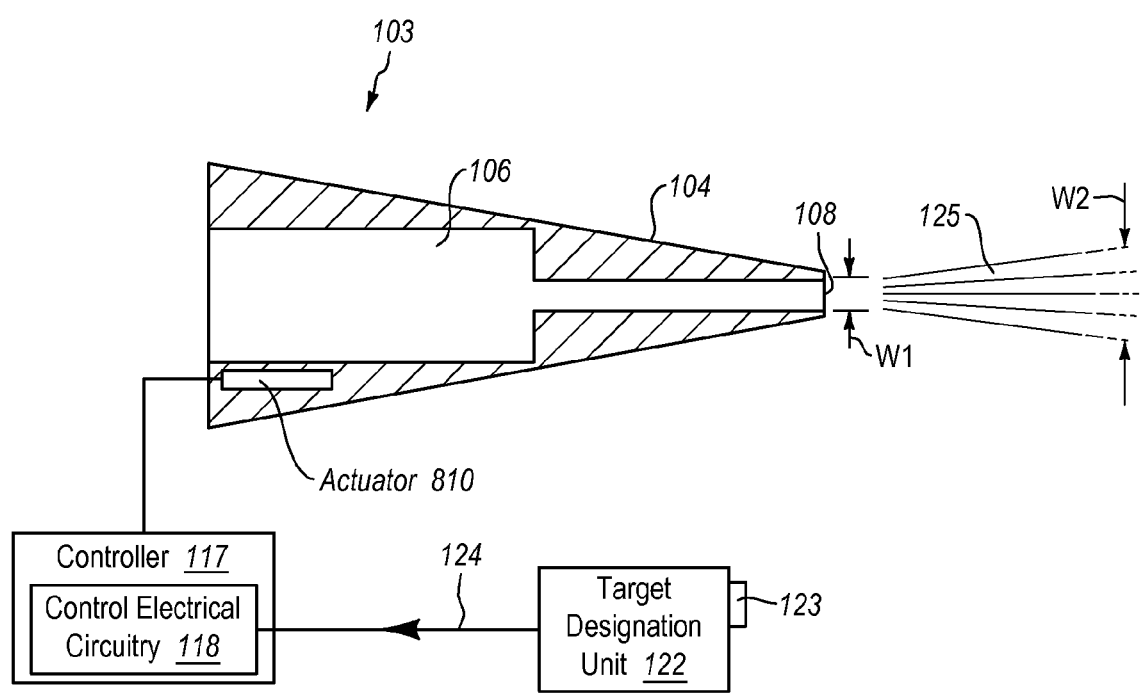
FIG. 8 is a partial schematic diagram of the fluid spraying apparatus shown in FIG. 1 in which a spray mechanism thereof includes an adjustable spray nozzle having an adjustable output orifice according to an embodiment.

FIG. 8 is a partial schematic diagram of the fluid spraying apparatus 100 shown in FIG. 1 in which the output orifice 108 of the adjustable spray nozzle 104 is adjustable according to an embodiment. The spraying device 103 includes a nozzle actuator 810 operably coupled to the adjustable spray nozzle 104 that is configured to alter a width W1 of the output orifice 108. In one or more embodiments, the nozzle actuator 810 may include at least one of a piezoelectric actuator, a shape-memory-alloy actuator, or an electromagnetic actuator that is configured to alter the width W1 of the output orifice 108 to thereby alter a width W2 of the spray 125 emanating therefrom. For example, the nozzle actuator 810 may selectively drive a needle assembly or other obstruction feature within the fluid delivery passageway 106 that either physically or operationally alters the width W1 of the output orifice 108. In another embodiment, the actuator 300 may increase or decrease the width W1 by deploying or un-deploying an aperture cover or other obstruction feature.

Figure 9:
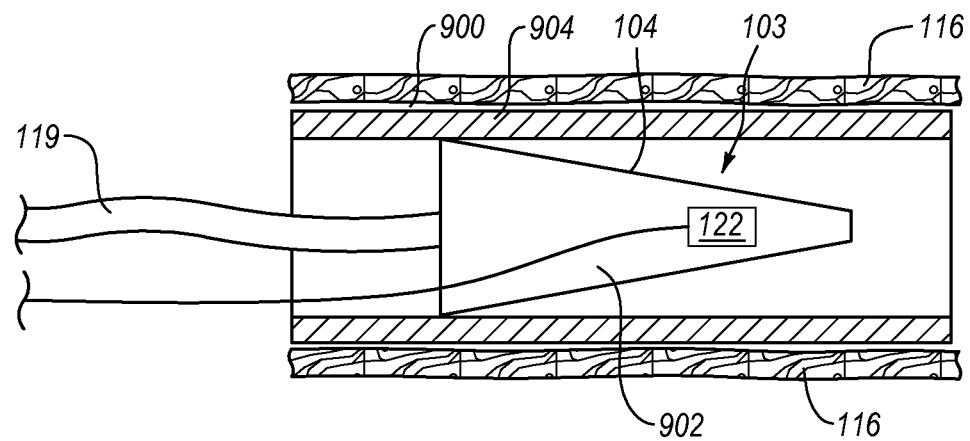
FIG. 9 is a partial schematic diagram of the fluid spraying apparatus shown in FIG. 1 in which a spray mechanism and the target designation unit thereof are integrated and disposed within a delivery catheter for deployment in a living subject according to an embodiment.

When the fluid spraying apparatus 100 is to be used for treating internal body tissue of the living subject 116, all or some components of the fluid spraying apparatus 100 may be compactly disposed in a delivery catheter. FIG. 9 is a partial schematic diagram of the fluid spraying apparatus 100 shown in FIG. 1 in which the spraying device 103 and the target designation unit 122 are integrated with each other for ease of delivery inside a body lumen 900 of the living subject 116 according to an embodiment. For example, the target designation unit 122 may be mounted to an exterior 902 of the adjustable spray nozzle 104 of the spraying device in a suitable position so that the distance sensor 122 has an appropriate "field-of-view" of the target region 114 of the living subject 116. The integrated assembly of the spraying device 103 and the target designation unit 122 may be compactly disposed within a delivery catheter 904 for deployment in the body lumen 900 of the living subject 116. For example, the delivery catheter 904 including the integrated assembly of the spraying device 103 and the distance sensor 122 may be deployed in the body lumen 900 using the Seldinger technique or other suitable technique. For example, the body lumen 900 may be defined by a wall of a vein, blood vessel, organ, or any other portion of the body of the living subject 116.

Figure 10:
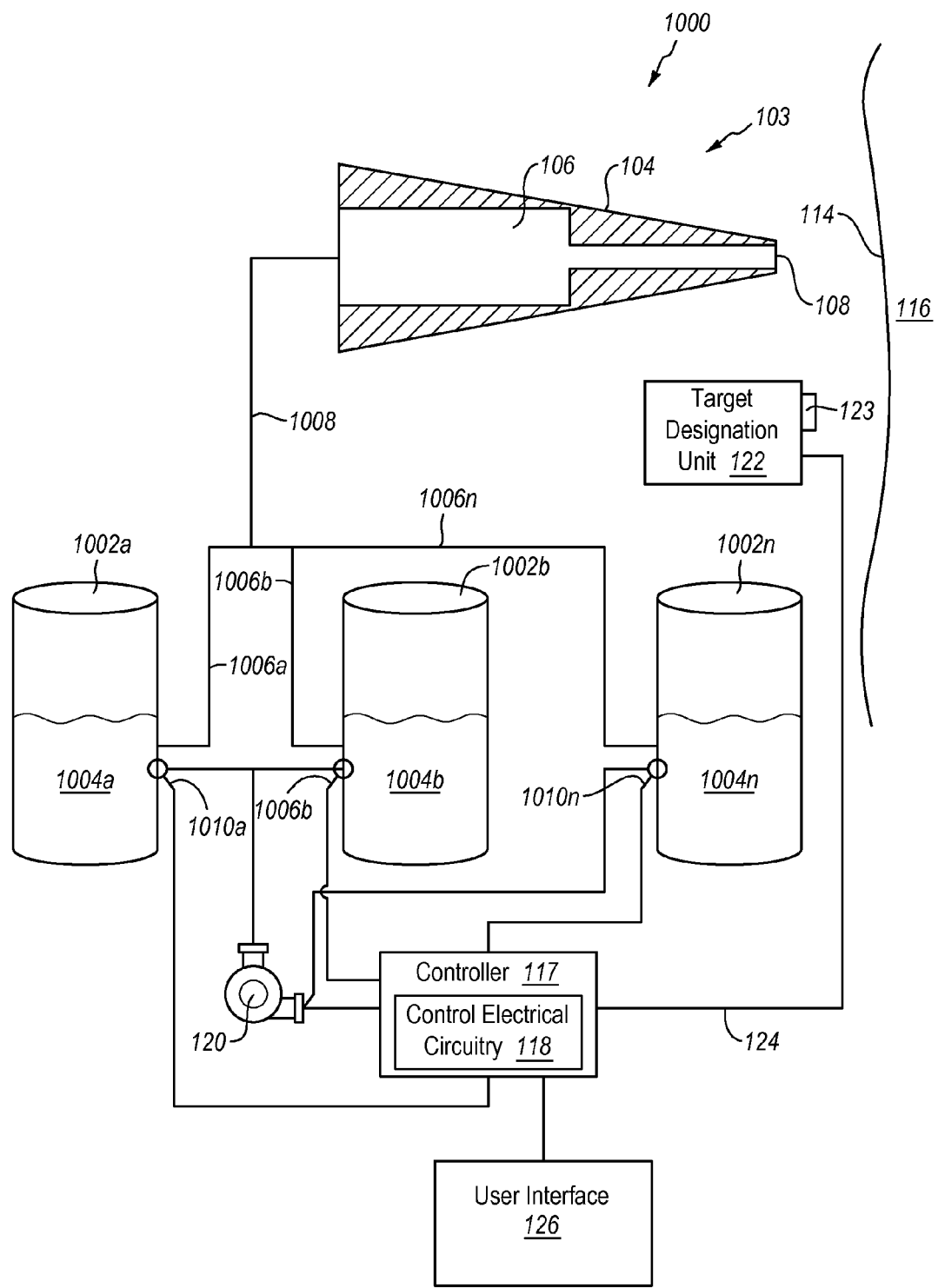

FIG. 10 is a schematic diagram of an embodiment of a fluid spraying apparatus 1000 including a plurality of reservoirs 1002a-1002n from which fluid may be selectively sprayed onto the target region 114 of the living subject 116. In the interest of brevity, components in both fluid spraying apparatuses 100 and 1000 that are identical or similar to each other have been provided with the same reference numerals and an explanation of their structure and function will not be repeated unless the components function differently in the fluid spraying apparatuses 100 and 1000.

Each of the plurality of reservoirs 1002a-1002n may hold a corresponding fluid 1004a-1004n therein that may have a different composition or maintained at a different temperature. For example, the fluids 1004a-1004n held in the corresponding reservoirs 1002a-1002n may be chosen from any of the fluids disclosed herein for the fluid 112, such as a liquid, a gas, an aerosol, a cryogen, or a fluid having a temperature greater than about 45° C. (i.e., a pyrofluid). Each of the reservoirs 1002a-1002n may be operably coupled to the pump 120. Fluid conduits 1006a-1006n may fluidly couple the fluids 1004a-1004n in the corresponding reservoirs 1002a-1002n to the fluid delivery passageway 106 of the adjustable spray nozzle 104 via a common fluid conduit 1008.

The pump 120 may be operably coupled to each of the reservoirs 1002a-1002n via corresponding valves 1010a-1010n. For example, each of the valves 1010a-1010n may be electronically-actuatable valves that may be selectively electronically actuated by the control electrical circuitry 118.

In operation, responsive to the one or more sensing signals 124 generated by the target designation unit 122 and optional user designation via the user interface 126, the control electrical circuitry 118 may selectively actuate the valves 1010a-1010n so that the fluids 1004a-1004n in the corresponding reservoirs 1002a-1002n may be selectively pumped by the pump 120 to the fluid delivery passageway 106 of the adjustable spray nozzle 104 via the common fluid conduit 1008.

For example, in an embodiment, the fluids 1004a-1004n may be sequentially sprayed onto the target region 114. In a more detailed embodiment, the fluid 1004a may be a first type of fluid (e.g., cryogen), while the fluids 1004b and 1004n may be different types of fluids (e.g., pyrofluids) maintained at different respective temperatures. In such an embodiment, the pyrofluids may first be sequentially sprayed onto a first sub-target region (e.g., a central region) of the target region 114 followed by spraying the cryogen onto a second sub-target region (e.g., a peripheral region that extends at least partially around the central region and at least partially defines the boundary of the target region 114) of the target region 114 or vice versa. In some embodiments, the control electrical circuitry 118 may determine the appropriate dimensions for the first and second sub-target regions.

Figure 11:
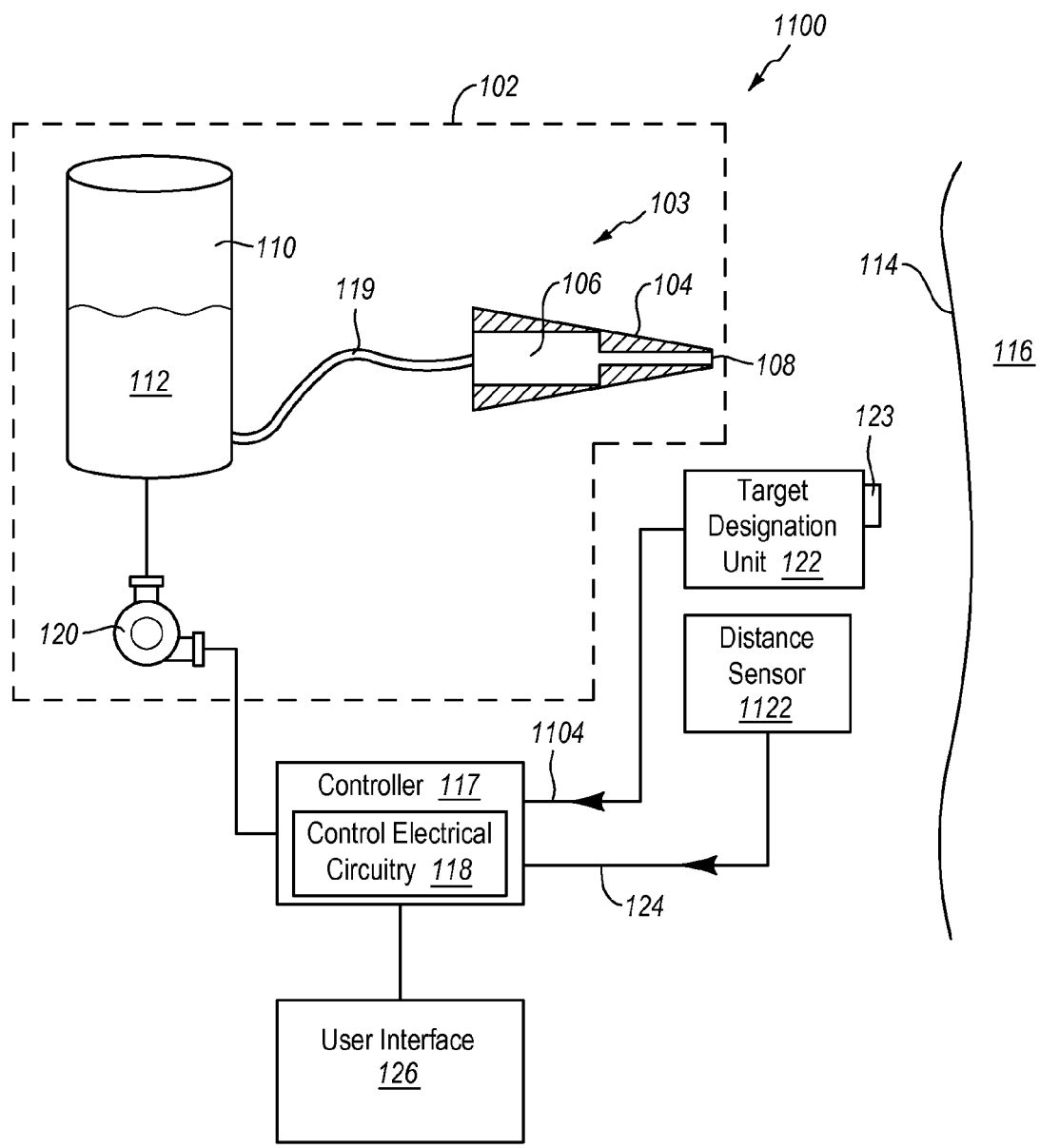

FIG. 11 is a schematic diagram of an embodiment of a fluid spraying apparatus 1100 that includes both at least one distance sensor and a target designation unit for assisting with accurate targeting of the target region 114 of the living subject 116. For example, the distance sensor may act in concert with the target designation unit to improve the accuracy of targeting of the target region 114 of the living subject 116. In the interest of brevity, components in both fluid spraying apparatuses 100 and 1100 that are identical or similar to each other have been provided with the same reference numerals and an explanation of their structure and function will not be repeated unless the components function differently in the fluid spraying apparatuses 100 and 1100.

Like the fluid spraying apparatus 100, the fluid spraying apparatus 1100 is suitable for spraying a medically suitable fluid onto a target region of a living subject for variety of uses, such as for treating or removing tissue of the living subject. However, the fluid spraying apparatus 1100 further includes at least one distance sensor 1122. The distance sensor 1122 is further operably coupled to the control electrical circuitry 118. For example, the distance sensor 1122 may be at least one of a passive distance sensor or an active distance sensor. Examples of suitable passive distance sensors include an image sensor, such as an electronic camera, machine vision system, or other suitable electronic imaging device. For example, such an image sensor may be positioned and configured to image subsurface features of the target region 114, such as vasculature of the target region 114, which can be affected by a fluid spray from the spraying device 103. Examples of suitable active distance sensors include an acoustic sensor that is configured to output an acoustic signal to the target region 114 and receive a reflected acoustic signal therefrom, an ultrasonic sensor that is configured to output an ultrasonic signal to the target region 114 and receive a reflected ultrasonic signal therefrom, an optical sensor that is configured to output an optical signal to the target region 114 and receive a reflected optical signal therefrom, or a radar device that is configured to output an electromagnetic signal to the target region 114 and receive a reflected electromagnetic signal therefrom.

The distance sensor 1102 is positioned and configured to sense information at least related to a distance that the spray mechanism 102 (e.g., the output orifice 108 of the adjustable spray nozzle 104) is from the target region 114 of the living subject 116 and output one or more sensing signals 124 to the control electrical circuitry 118 indicative (e.g., encoding) of the information at least related to the distance.

In operation, in addition to target designation unit 122 enabling designation of the target region 114 as discussed above with respect to FIG. 1, the distance sensor 1102 senses information at least related to a distance that the spray mechanism 102 is from the target region 114 of the living subject 116 and outputs the one or more distance sensing signals 1104 to the control electrical circuitry 118 indicative of the information at least related to the distance. The control electrical circuitry 118 may determine one or more operational characteristics of the spray mechanism 102 (e.g., adjustable spray nozzle 104, at least one reservoir 110, or the pump 120) to be adjusted at least partially based on the information, adjusts the one or more operational characteristics of the spray mechanism 102 at least partially based on the determined one or more operational characteristics, and directs the adjusted spray mechanism 102 configured with the one or more adjusted operational characteristics to spray the fluid 112 as the spray 125 onto the target region 114 responsive to the pump 120 delivering the fluid 112 to the spray mechanism 102. For example, the one or more operational characteristics include at least one of pressure of the spray 125, droplet size of the spray 125, or geometry of the spray 125.

As further explained below, responsive to the one or more distance sensing signals 1104, the control electrical circuitry 118 may direct altering a number of different operational characteristics of the spray mechanism 102. For example, during operation, the control electrical circuitry 118 may direct the adjustable spray nozzle 104 to alter a spray width of the spray 125 responsive to receiving the one or more sensing signals 124. As another example, during operation, the control electrical circuitry 118 may direct the pump 120 to alter a fluid pressure of the fluid 112 sprayed therefrom as the spray 125 responsive to receiving the one or more sensing signals 124. Altering the fluid pressure may be effected by increasing or decreasing the pressure exerted on the fluid 112 in the reservoir 110 by the pump 120. As yet another example, during operation, the control electrical circuitry 118 may direct the adjustable spray nozzle 104 to alter a fluid focus thereof responsive to receiving the one or more sensing signals 124. As a further example, during operation, the control electrical circuitry 118 may direct the spray mechanism 102 to alter a droplet size of the spray 125 responsive to receiving the one or more sensing signals 124 by increasing or decreasing the pressure exerted on the fluid 112 in the reservoir 110 by the pump 120. As yet a further example, during operation, the control electrical circuitry 118 may direct adjusting the adjustable spray nozzle 104 to substantially maintain a target arrival diameter of the spray 125 responsive to receiving the one or more sensing signals 124.

In an embodiment, the control electrical circuitry 118 is configured to direct the spray mechanism 102 to stop spraying the fluid 112 responsive to a specified operational condition. For example, the specified operational condition includes at least one of spray time, the distance being outside a specified range as sensed by the distance sensor 1122, or the distance changing at a rate exceeding a maximum rate as sensed by the distance sensor 1122. In other embodiments, the control electrical circuitry 118 directs the spray mechanism 102 to intermittently spray the fluid 112 onto the target region 114. As previously discussed, the specified operational conditions may be pre-programmed into the control electrical circuitry 118 or set by the user.

Figure 12:
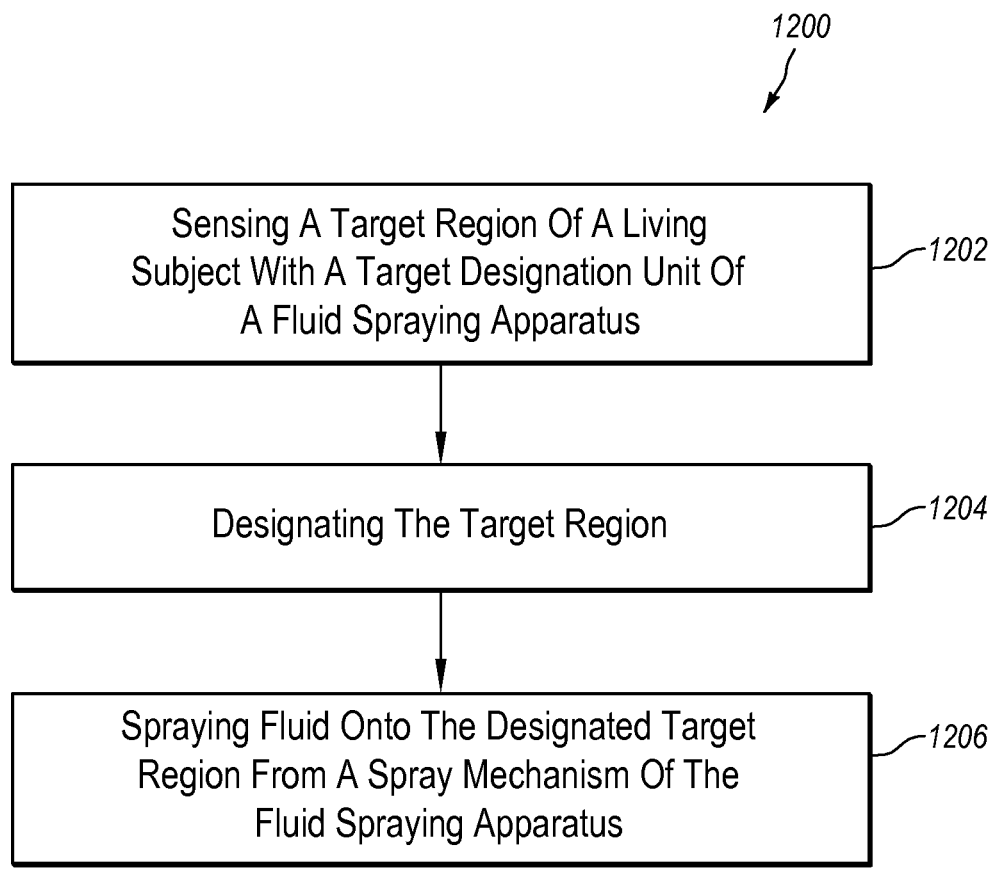

FIG. 12 is a flow diagram of an embodiment of an operating method 1200 that may be implemented using any of the fluid spraying apparatuses disclosed herein, such as the fluid spraying apparatuses described in relation to FIGS. 1-11. The method 1200 is directed to a method of designating a target region (e.g., an internally or externally located region of a living subject) and spraying fluid onto the designated target region from a spray mechanism of a fluid spraying apparatus. The method 1200 includes an act 1202 of sensing a target region of a living subject with a target designating unit. The method 1200 further includes an act 1204 of designating the target region, such as via a computer user interface (e.g., user interface 126). The method 1200 further includes an act 1206 of spraying fluid onto the target region so designated from a spray mechanism of a fluid spraying apparatus. For example, as previously discussed, the target region may be internally or externally located on the living subject.

In an embodiment, the act 1202 of sensing may include sensing an indicator or a feature of the target region, such as an ink indication on the target region or an indication designated via light output from a lighting device (e.g., the lighting device 500). In an embodiment, the act 1202 of sensing may include imaging the target region with an image sensor, such as an electronic camera or a machine vision system. In some embodiments, the image sensor and related control electrical circuitry may recognize the target region by at least one feature thereof.

In an embodiment, the act 1206 of spraying fluid onto the target region so designated from a spray mechanism of a fluid spraying apparatus occurs substantially automatically responsive to the designating the target region. In an embodiment, the act 1206 of spraying fluid onto the target region so designated from a spray mechanism of a fluid spraying apparatus includes directing the fluid at a selected number of regions within the target region, directing the fluid at a single region within the target region, or substantially continuously sweeping the fluid over the target region.

In an embodiment, the act 1204 of designating a target region includes specifying a sub-target region (e.g., via a user interface) that at least partially defines the target region, and the act 1206 of spraying fluid onto the target region so designated includes spraying the fluid within the sub-target region.

In an embodiment, the act 1202 of sensing a target region includes sensing a temperature of each of a plurality of regions of the living subject that includes the target region, and the act 1204 of designating the target region includes selecting the target region from among the plurality of regions at least partially based on the temperature thereof. In another embodiment, the act 1202 of sensing a target region includes sensing a temperature of the target region, and the act 1206 of spraying fluid onto the target region so designated from a spray mechanism of a fluid spraying apparatus includes spraying the fluid onto the target region until a selected temperature of the target region is sensed with the target designating device. In another embodiment, the act 1202 of sensing a target region includes sensing a temperature of the target region, and the act 1206 of spraying fluid onto the target region so designated from a spray mechanism of a fluid spraying apparatus includes imposing a selected temperature profile on the target region, such as three-dimensional temperature profile, a temperature-time profile, a temperature-depth profile, or a temperature-time-depth profile.

In an embodiment, the act 1206 of spraying fluid onto the target region so designated from a spray mechanism of a fluid spraying apparatus includes selectively spraying different types of cryogens or other fluids onto different regions of the target region.

Figure 13:
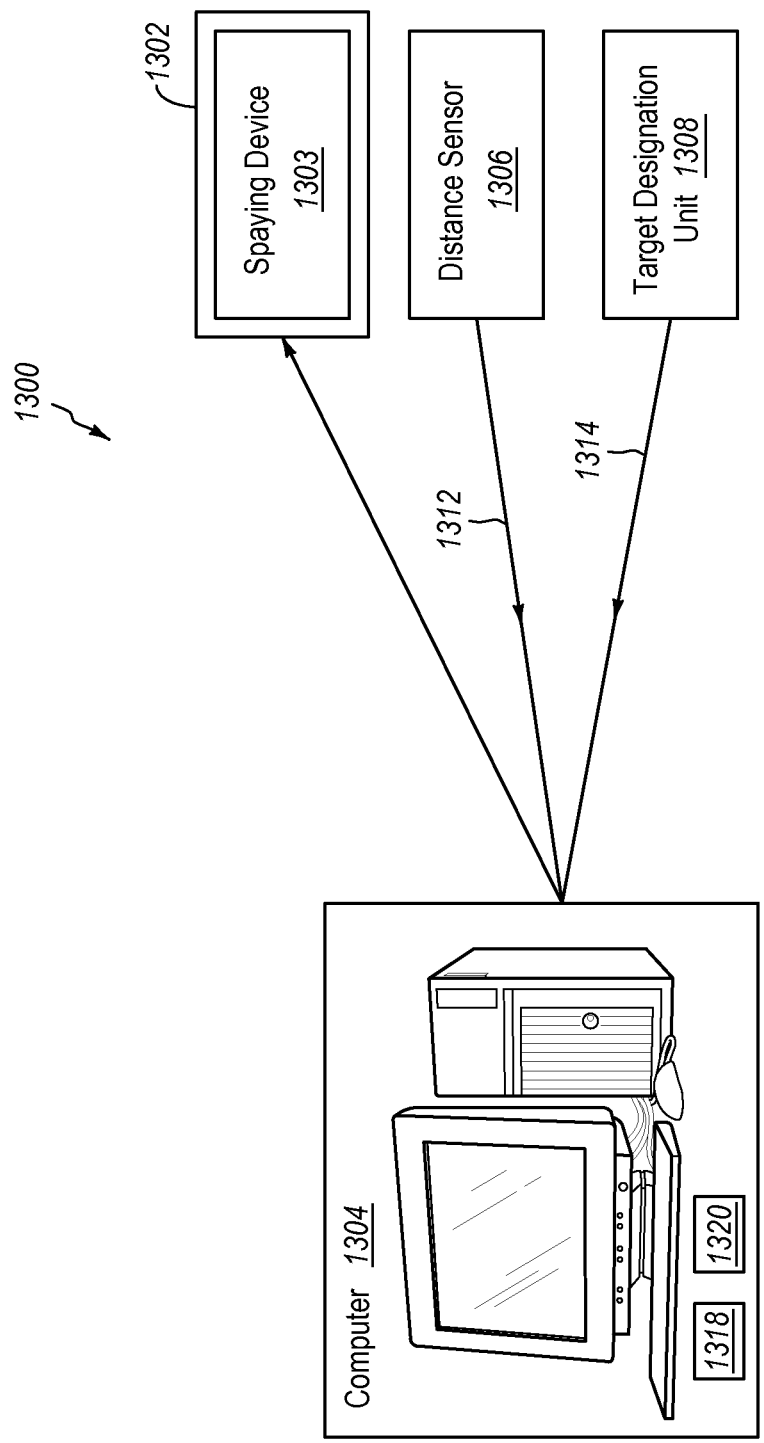

FIG. 13 is a schematic diagram of an embodiment of a system 1300 including a fluid spraying apparatus 1302 having a spraying device 1303 and a computer 1304 for controlling the fluid spraying apparatus 1302. The system 1300 further includes an optional distance sensor 1306 and a target designation unit 1308. The distance sensor 1306 and the target designation unit 1308 may be structured and function the same or similar to those components previously described in relation to FIGS. 1, 2, 4-6, 10, and 11. For example, the distance sensor 1306 may output one or more distance sensing signals 1312 indicative of a distance that the fluid spraying apparatus 1302 is from a target region, and the target designation unit 1308 may output one or more target sensing signals 1314. The spraying device 1303 may be configured as any of the spraying devices disclosed herein.

The distance sensor 1306 and the target designation unit 1308 may be remote from the fluid spraying apparatus 1302 or may be integrated with the fluid spraying apparatus 1302. Additionally, the distance sensor 1306 and the target designation unit 1308 may be wirelessly coupled or electrically coupled via a wired connection to the computer 1304.

The computer 1304 may be any suitable desktop computer, laptop computer, or other suitable computing platform, which is operably coupled to the fluid spraying apparatus 1302, the optional distance sensor 1306, and the target designation unit 1308. The computer 1304 may include at least one processor 1318 and memory 1320 storing instructions that when executed by the processor 1318 activates or directs the fluid spraying apparatus 1302 (e.g., the spraying device 1303 of the fluid spraying apparatus 1302) responsive to receiving the optional one or more distance sensing signals 1312 and the one or more target sensing signals 1314.

In an embodiment, the computer 1304 may be remote from the fluid spraying apparatus 1302, such as in another room or another section of the same room. In an embodiment, the computer 1304 may be integrated with the fluid spraying apparatus 1302 similar to the manner in which the control electrical circuitry 118 forms part of the fluid spraying apparatus 100.

The instructions stored in the memory 1320 may be for implementing any of the targeting, selection, or designation of a target region and directing of the spraying device 1303 for spraying fluid onto the target region so designated. For example, the memory 1320 may include instructions that when executed by the at least one processor 1318 cause the fluid spraying apparatus 1302 to perform any of the methods described in connection with FIG. 12. As such, the control electrical circuitry 118 previously discussed may be considered to constitute part of or all of the processor 1318 and the memory 1320. For example, responsive to the one or more distance sensing signals 1312, the computer 1304 may direct altering a number of different operational characteristics of the fluid spraying apparatus 1302. For example, responsive to the one or more target sensing signals 1314, the computer 1304 may allow the user to designate the target region and direct operation of the fluid spraying apparatus 1302 to spray the target region so designated.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A fluid spraying apparatus, comprising:
   a target designation unit including a target sensor configured to sense a target region of a living subject;
   a spray mechanism including,
      at least one reservoir configured to hold fluid; and
      a spraying device including an adjustable spray nozzle having a fluid delivery passageway therethrough operably coupled to the at least one reservoir and terminating in a single output orifice, the spraying device configured to spray the fluid in the at least one reservoir as a focused spray onto the target region through the single output orifice; and
   an obstruction feature deployable within the fluid delivery passageway or over the single output orifice to alter a width of the single output orifice; and
   a nozzle actuator configured to deploy the obstruction feature;
   a controller including control electrical circuitry operably coupled to the spray mechanism, the nozzle actuator, and the target designation unit, the control electrical circuitry configured to control the spray mechanism responsive to the target sensor sensing the target region including directing the nozzle actuator to controllably adjust the width of the single output orifice of the adjustable spray nozzle by deploying, or undeploying, the obstruction feature to adjust at least one spray characteristic of the fluid sprayed therefrom; and
   a delivery catheter housing at least the target designation unit and the spraying device therein.

2. The fluid spraying apparatus of claim 1, wherein the control electrical circuitry is configured to automatically activate the spray mechanism responsive to the target sensor sensing the target region.

3. The fluid spraying apparatus of claim 1, further including a user interface operably coupled to the control electrical circuitry, the user interface configured to receive input designating the target region and communicate the input to the control electrical circuitry.

4. The fluid spraying apparatus of claim 3, wherein:
   the target sensor includes at least one image sensor configured to identify the target region and communicate the identified target region to the control electrical circuitry; and
   the user interface is configured for a user to designate the identified target region.

5. The fluid spraying apparatus of claim 1, wherein the target sensor includes at least one image sensor configured to detect an indicator or a feature that at least partially defines the target region.

6. The fluid spraying apparatus of claim 1, wherein:
   the target sensor includes a motion sensor configured to sense motion of the spray mechanism and output one or more motion signals encoding data related to the sensed motion to the control electrical circuitry; and
   the control electrical circuitry includes memory configured to store the data, the control electrical circuitry configured to instruct the spray mechanism to direct spraying the fluid responsive to the data.

7. The fluid spraying apparatus of claim 1, wherein the control electrical circuitry is configured to determine a sub-target region that at least partially defines the target region.

8. The fluid spraying apparatus of claim 1, wherein the control electrical circuitry is configured to direct the spray mechanism to spray a selected number of sub-regions within the target region.

9. The fluid spraying apparatus of claim 1, wherein the control electrical circuitry is configured to direct the spray mechanism to spray the target region with the fluid as a substantially continuously swept spray.

10. The fluid spraying apparatus of claim 1, wherein the control electrical circuitry is configured to control the spray mechanism to substantially maintain a spray of the fluid directed at the target region.

11. The fluid spraying apparatus of claim 1, wherein:
    the target sensor includes a temperature sensor configured to sense a temperature of each of a plurality of regions of the living subject including the target region and communicate the temperature of each of the plurality of regions to the control electrical circuitry; and
    the control electrical circuitry is configured to select the target region from among the plurality of regions at least partially based on the temperature thereof.

12. The fluid spraying apparatus of claim 11, wherein the temperature sensor is remote from the spray mechanism.

13. The fluid spraying apparatus of claim 1, wherein:
    the target sensor includes a motion sensor configured to sense motion of the spray mechanism and output one or more motion signals to the control electrical circuitry; and
    the control electrical circuitry is configured to instruct the spray mechanism to direct the spray of the fluid responsive to the one or more motion signals.

14. The fluid spraying apparatus of claim 1, wherein the fluid includes cryogen or a fluid having a temperature greater than 45° C.

15. The fluid spraying apparatus of claim 1, wherein:
    the at least one reservoir includes a plurality of cryogen reservoirs, each of the plurality of cryogen reservoirs including a different type of cryogen therein;
    a plurality of valves each of which is associated with a corresponding one of the plurality of cryogen reservoirs and configured to selectively fluidly couple the different type of cryogen from the corresponding one of the plurality of cryogen reservoirs to the spray mechanism; and
    the control electrical circuitry is operably coupled to the plurality of valves, the control electrical circuitry configured to selectively activate the plurality of valves and direct the spray mechanism to spray the different type of cryogen from a first one of the plurality of cryogen reservoirs onto a first sub-target region of the target region and the different type of cryogen from a second one of the plurality of cryogen reservoirs onto a second sub-target region of the target region.

16. The fluid spraying apparatus of claim 15 wherein the first sub-target region includes a central portion and the second sub-target region includes a peripheral portion.

17. The fluid spraying apparatus of claim 15, wherein the spray mechanism is configured to selectively direct the spray of the different type of cryogen from the first one of the plurality of cryogen reservoir onto the first sub-target region of the target region and the spray of the different type of cryogen from the second one of the plurality of cryogen reservoir onto the second sub-target region of the target region.

18. The fluid spraying apparatus of claim 1, wherein:
    the spray mechanism includes a heating element disposed in the at least one reservoir and configured to heat the fluid; and the control electrical circuitry operably coupled to the heating element, and configured to direct the heating element to heat the fluid.

19. The fluid spraying apparatus of claim 1, wherein:
the spray mechanism includes a cooling element disposed in the at least one reservoir and configured to cool the fluid; and
the control electrical circuitry operably coupled to the cooling element, and configured to direct the cooling element to cool the fluid.

20. The fluid spraying apparatus of claim 1, further including:
a distance sensor configured to sense information at least related to a distance to the target region of the living subject and output one or more signals encoding the information; and
wherein the control electrical circuitry is operably coupled to the distance sensor, and configured to direct adjusting spray mechanism responsive to the one or more signals.

21. The fluid spraying apparatus of claim 20, wherein, responsive to the one or more signals, the spray mechanism is configured to adjust at least one of a spray width of the fluid sprayed, a fluid pressure of the fluid sprayed, a fluid focus of the adjustable spray nozzle, the single output orifice of the adjustable spray nozzle, or a droplet size of the fluid sprayed.

22. The fluid spraying apparatus of claim 1, wherein the control electrical circuitry is configured to adjust an operational characteristic that the spraying device sprays the fluid responsive to the target designation unit sensing the fluid impacts outside the target region.

23. The fluid spraying apparatus of claim 1, wherein the at least one spray characteristic includes at least one of a fluid focus of the fluid sprayed from the adjustable spray nozzle or a droplet size of the fluid sprayed from the adjustable spray nozzle.

24. The fluid spraying apparatus of claim 1, wherein the adjustable spray nozzle includes an atomizing adjustable spray nozzle or a pressure-swirl spray nozzle.

25. The fluid spraying apparatus of claim 1, wherein the obstruction feature includes a needle.

26. The fluid spraying apparatus of claim 1, wherein the obstruction feature includes a cover.

27. The fluid spraying apparatus of claim 1, wherein the adjustable spray nozzle includes the nozzle actuator.

28. A system, comprising:
a target designation unit including a target sensor configured to sense a target region of a living subject;
a distance sensor configured to sense information at least related to a distance to the target region of the living subject and output one or more signals encoding the information;
a fluid spraying apparatus operably coupled to the target designation unit, the fluid spraying apparatus having a spray mechanism including,
at least one reservoir configured to hold fluid;
a pump operably coupled to the at least one reservoir;
a spraying device including an adjustable spray nozzle having a fluid delivery passageway therethrough operably coupled to the at least one reservoir and terminating at a single output orifice, the spraying device configured to spray the fluid in the at least one reservoir onto the target region through the single output orifice;
an obstruction feature deployable within the fluid delivery passageway or over the single output orifice; and;
a delivery catheter housing at least the target designation unit and the spraying device therein; and
a computer operably coupled to the spray mechanism, the target designation unit, and the distance sensor, the computer including memory storing instructions for controlling the spray mechanism responsive to the target sensor sensing the target region and the one or more signals including controllably adjusting the pump or obstruction feature of the adjustable spray nozzle to adjust at least one spray characteristic of the fluid sprayed therefrom, wherein the at least one characteristic includes at least one of a spray width of the fluid sprayed, a fluid focus of the adjustable spray nozzle, a width of the single output orifice of the adjustable spray nozzle, or a droplet size of the fluid sprayed.

29. A fluid spraying apparatus, comprising:
a target designation unit including a target sensor configured to sense a target region of a living subject, the target sensor including a temperature sensor configured to sense a temperature of each of a plurality of regions of the living subject including the target region;
a spray mechanism including,
at least one reservoir configured to hold fluid; and
a pump operably coupled to the at least one reservoir;
a spraying device operably coupled to the at least one reservoir, the spraying device configured to spray the fluid in the at least one reservoir onto the target region; and
a controller including control electrical circuitry operably coupled to the spray mechanism and the target designation unit, the control electrical circuitry configured to communicate with the temperature sensor to receive the temperature sensed in each of the plurality of regions and to select the target region from among the plurality of regions at least partially based on the temperature thereof, the control electrical circuitry being configured to activate the pump of the spray mechanism to pump the fluid through the spray mechanism responsive to selecting the target region.

30. A fluid spraying apparatus, comprising:
a target designation unit including a target sensor configured to sense a target region of a living subject and a first sub-target region and a second sub-target region therein;
a spray mechanism including,
a plurality of cryogen reservoirs, each of the plurality of cryogen reservoirs including a different type of cryogen therein;
a plurality of valves each of which is associated with a corresponding one of the plurality of cryogen reservoirs and configured to selectively fluidly couple the different type of cryogen from the corresponding one of the plurality of cryogen reservoirs to the spray mechanism; and
a spraying device operably coupled to the plurality of cryogen reservoirs, the spraying device configured to spray the cryogen in the plurality of cryogen reservoirs onto the target region; and
a controller including control electrical circuitry operably coupled to the spray mechanism including the plurality of valves and the target designation unit, the control electrical circuitry configured to control the spray mechanism responsive to the target sensor sensing the target region and configured to selectively activate the plurality of valves and direct the spray mechanism to spray the different type of cryogen from a first one of the plurality of cryogen reservoirs onto the first sub-target region of the target region and the different type of cryogen from a second one of the plurality of cryogen reservoirs onto the second sub-target region of the target region responsive to the target sensor sensing the first sub-target region and the second sub-target region.

31. A fluid spraying apparatus, comprising:
a target designation unit including a target sensor configured to sense at least one characteristic of a target region of a living subject;
a spray mechanism including,
   at least one reservoir configured to hold fluid;
   a spraying device operably coupled to the at least one reservoir, the spraying device configured to spray the fluid in the at least one reservoir onto the target region;
   a fluid temperature control element disposed in the at least one reservoir and including at least one of a heating element configured to heat the fluid or a cooling element configured to cool the fluid; and
a controller including control electrical circuitry operably coupled to the spray mechanism and the target designation unit, the control electrical circuitry configured to control the spray mechanism responsive to the target sensor sensing the at least one characteristic of the target region and to at least activate the fluid temperature control element to adjust a temperature of the fluid by heating or cooling the fluid to a selected temperature responsive to the sensed at least one characteristic of the target region.

* * * * *